United States Patent [19]

Fackler

[11] Patent Number: 4,760,747

[45] Date of Patent: Aug. 2, 1988

[54] LIQUID SAMPLING AND MEASURING DEVICE

[75] Inventor: Dale J. Fackler, Boise, Id.

[73] Assignee: Petro Sales Corporation, Boise, Id.

[21] Appl. No.: 35,490

[22] Filed: Apr. 6, 1987

[51] Int. Cl.$^4$ .............................................. G01N 1/12
[52] U.S. Cl. ............................. 73/864.65; 73/864.63;
33/126.4 R
[58] Field of Search ........... 73/864.65, 864.63, 864.64,
73/864.66, 864.67; 33/126.4 R, 126.4 A

[56] References Cited

U.S. PATENT DOCUMENTS

| | | | |
|---|---|---|---|
| 2,137,128 | 11/1938 | Blake | 73/864.65 |
| 2,622,435 | 12/1952 | Lucas et al. | 73/864.65 X |
| 3,097,532 | 7/1963 | Brown et al. | 73/864.65 |
| 3,169,322 | 2/1965 | Milo | 73/864.65 X |
| 3,390,463 | 2/1968 | Hirsch | 73/864.65 X |
| 4,326,427 | 4/1982 | Ueberschaer | 73/864.65 |

Primary Examiner—Tom Noland
Attorney, Agent, or Firm—Paul F. Horton

[57] ABSTRACT

A liquid sampling and measuring device including a tubular casing, preferably constructed of transparent material, for holding a liquid and a valve. The tubular casing includes, at its lowermost end, a liquid conduction port for permitting liquid to flow into and from the casing. The valve, located within the casing, includes a spring biased piston provided with a port sealing member. A foot member, connected to the piston and extending through the port, operates, under pressure downwardly applied to the casing, to cause the sealant piston to retract against the bias of the spring. Cooperating cam members cause the piston to rotate and cooperating retention members on the piston and within the casing holds the piston in a retracted, open position. Pressure applied once again to the foot member causes further rotation of the piston to return the piston to an extended, closed position for sealing the port. Detachable tubular sections permit convenient storage of the device, while allowing tubular extensions for any desired depth.

12 Claims, 3 Drawing Sheets

LIQUID SAMPLING AND MEASURING DEVICE

BACKGROUND OF THE INVENTION

1. Field of the Invention

This invention relates, in general, to tubular liquid sampling and measuring devices, and, more particularly, to tubular devices which include a valve member which may be opened or closed by contact of the device on the bottom of a tank or reservoir.

2. Description of the Prior Art

The desirability of utilizing tubular structures for sampling and measuring liquids has long been recognized. It is important to the seller or dispenser of liquids, such as gasoline, to know if any contaminants, such as water, have entered the tank and, if so, what those contaminants might be. It is also important to know the amount of such contaminants, as determined by a core sample of the liquid and to also determine the total amount of liquid in the tank.

Many of the prior art sampling and measuring devices, as typified by U.S. Pat. No. 3,390,463, issued to E. Hirsch, are incapable of being opened only at the bottom of a tank to take a sample or remove contaminated liquid only. Such devices must be opened prior to immersion into the liquid and then triggered into a closed position.

Other devices, such as U.S. Pat. No. 4,346,519, issued to A. Milo, have measuring sticks to determine the depth of the liquid, and hence do not take full core samples and cannot be both opened and closed by contact with the bottom of the tank, but rather have separate cords running to an external cord holder for opening a valve.

The sampling and measuring device of the present invention overcomes these deficiencies by providing a liquid sampling and measuring device having a valve which can be alternately opened or closed by simply engaging the bottom of a storage tank or reservoir with the device and by providing a tubular casing which can be readily extended to obtain a core sample of the entire fluid depth.

SUMMARY OF THE INVENTION

It is therefore a primary object of the present invention to provide a liquid sampling and measuring device which has a valve which can be opened or closed merely by compression of a valve foot on the bottom of a tank.

It is also an object of the present invention to provide a liquid sampling and measuring device which may be immersed into a liquid contained within a tank with the valve closed and then to open the valve, once it engages the bottom of the tank, to collect a bottom sample only.

More particularly, it is an object of the present invention to provide a liquid sampling and measuring device which includes a valve piston which is rotated to open and closed positions by cooperating cam members.

Another object of the present invention is to provide a liquid sampling and measuring device which includes tubular sections for extending or shortening the device for use on tanks of differing depths and to provide convenient storage of the device.

Additional objects and advantages will become apparent and a more thorough and comprehensive understanding may be had from the following description taken in conjunction with the accompanying drawings forming a part of this specification.

DETAILED DESCRIPTION OF THE INVENTION

Figure 1:
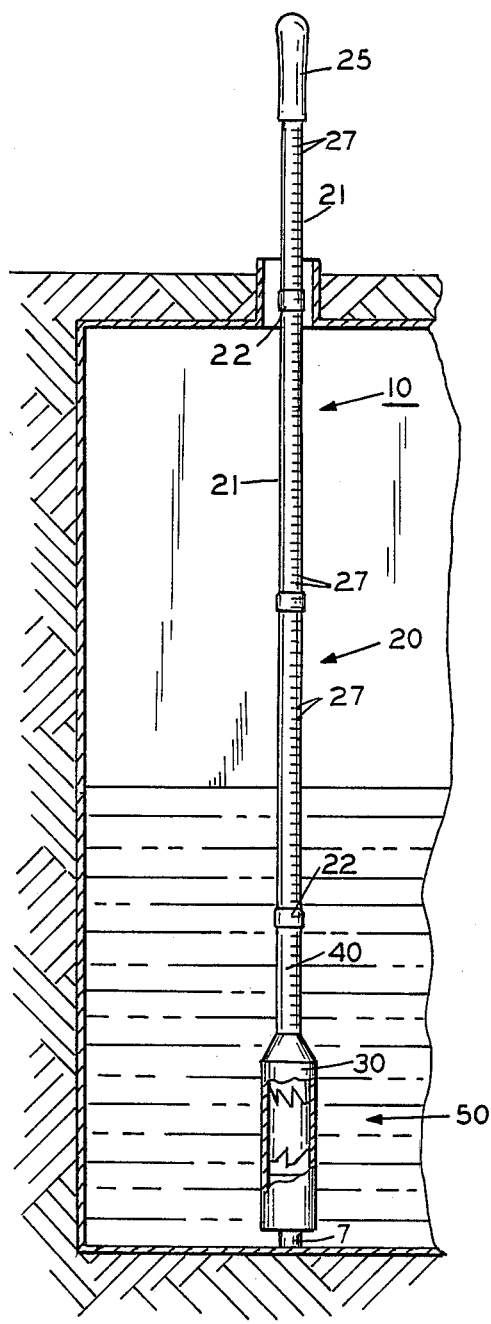
FIG. 1 is a side view of a preferred embodiment of the invention, showing use in an underground storage tank.

Referring now to the drawings and to FIG. 1, in particular, an embodiment to be preferred of a liquid sampling and measuring device 10, made according to the present invention is disclosed. Device 10 includes a tubular casing, designated generally by the numeral 20 and valve means, designated generally by the numeral 50. The valve means includes all members of the device which cooperate in the opening and closing of port 38 of the tubular casing, as hereinafter described.

Tubular casing 20 includes a first tubular casing 30, a second tubular casing 40, sealingly engaging the first casing, and may also include a selected number of graduated liquid level tubes 21 which are connected to casing 40 and to each other in sealing engagement with one another by any conventional means such as threaded or twist-lock couplings, designated generally by the numeral 22. A handle 25 may be affixed to the uppermost tube 21. The number of graduated tubes 21 in a complete assembly is determined by the desired length of the assembly or the depth of the liquid being measured or sampled. Graduations 27 are consecutively higher on each added section of tubing. Tubing 20 may be constructed of a transparent plastic type material, such as polyethylene, the particular material being determined by the corrosive action of the liquids being sampled or measured. Liquid is controlled from entering or exiting device 10 by the interaction of second tubular casing 40, first tubular casing 30 and by valve means 50.

Figure 2:
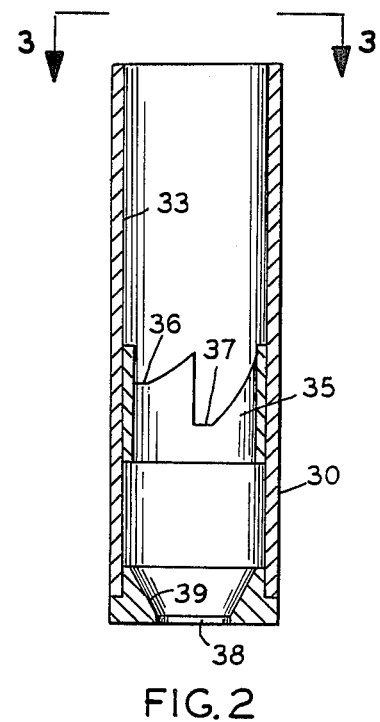
FIG. 2 is a cross sectional view of the first tubular casing of the invention.
Figure 3:
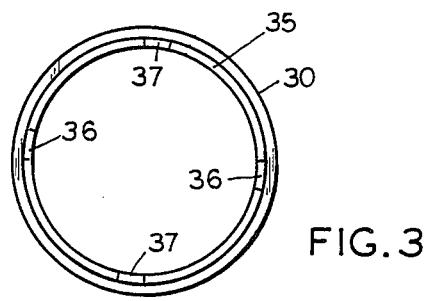
FIG. 3 is a cross sectional view taken along lines 3—3 of FIG. 2.
Figure 10:
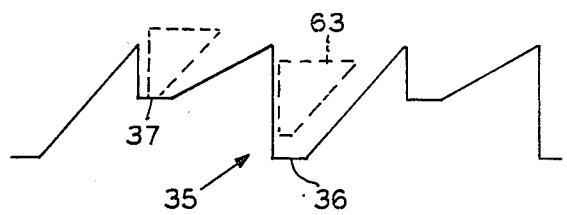
FIG. 10 is an expanded detail of the piston elevation retention means of the invention.

First tubular casing 30, seen in cross section in FIG. 2, includes a valve seat 39 surrounding a liquid conduction port 38. On the inner surface 33 of tubular casing 30 is affixed piston elevation retention means 35, which is preferably in the form of a circular cam about the inner periphery of the casing, as shown in detail in FIG. 3 and FIG. 10. The cam provides two levels of lug stops 36 and 37, about its saw-like shape. Lug stops 36, being at a lower level than stops 37, permit piston 60 to be fully extended to seal port 38 of first casing 30 as lugs 63 of the piston engage lug stops 36. Lug stops 37 cause the piston to be held in a retracted position, as lugs 63 of the piston engage lug stops 37, to open port 38, as will hereinafter be more fully explained.

Second tubular casing 40 is preferably separable from first tubular casing 30 for maintenance and assembly purposes and is sealed to the first casing by any conventional means. Second casing 40 serves three primary functions. First, it serves as a connecting device to connect the larger diameter first casing 30 to the graduated liquid level tubes 21. Second, the casing includes on its lowermost terminal end, as shown to advantage in FIGS. 4, 6, 7, and 8, a first cam member 42, defining a series of adjacent inclined planes, in saw-tooth form. Cam member 42 interacts with a mating second cam 65 which is located on the uppermost terminal end of piston 60. The interaction of the caming surfaces of these two cams cause a rotation of piston 60 as will also hereinafter be more fully described. Third, casing 40 includes a spring compression shaft retention means in the form of a cap 46 which is held in place at the longitudinal axis of the casing by a spark resistant metal retaining pin 47 of an alloy which resists the corrosive action of the liquid being sampled or measured. The cap interacts with spring compression shaft 71 as will be described in the operation of device 10.

Figure 5:
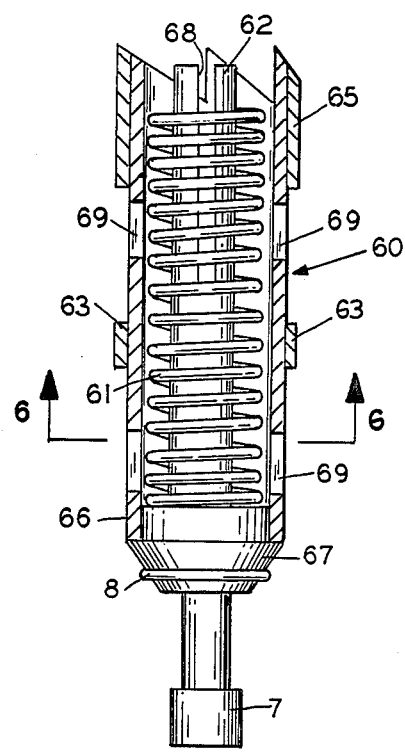
FIG. 5 is a cross sectional view of the piston assembly.
Figure 4:
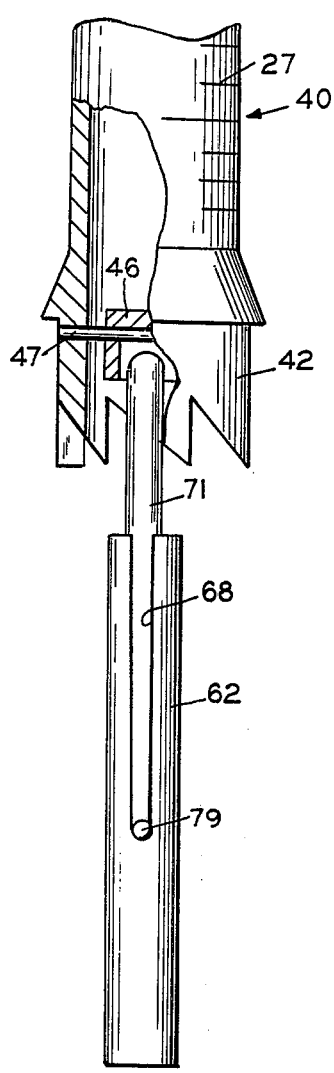
FIG. 4 is a partial sectional view of the second tubular casing showing the spring compression shaft and spring guide shaft in relationship to the second tubular casing.
Figure 6:
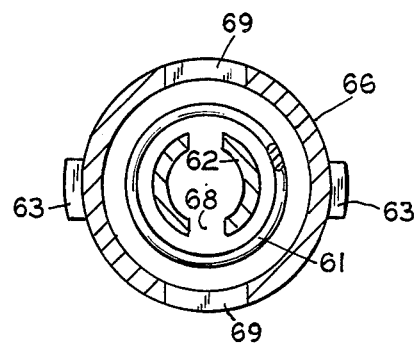
FIG. 6 is a sectional view taken along lines 6—6 of FIG. 5.

Flow control piston 60, shown in FIG. 5, is central to the operation of the device. At the lowermost end of the piston is a foot 7 made of rubber or other cushion-like material to prevent damage to the surface with which it comes in contact, as for example the bottom 1 of the tank shown in FIG. 1. Foot 7 connects to a seal head 67 which defines the bottom wall of the piston. Seal head 67 contains a groove to accommodate an O-ring seal 8 of rubber or other material not subject to corrosion by the liquid. The tubular wall 66 of piston 60 includes a plurality of apertures 69, as may be seen in FIG. 6, to allow liquids to flow to the inside of the piston. The apertures are required to allow the flow of liquid around the piston at the point where the piston and piston retention means 35 meet. Lugs 63 are preferably two in number and are oppositely disposed on the exterior surface of the piston. The lugs may be provided with an inclined plane which may engage the inclined plane of piston retention means 35. Second cam 65, located at the top of the piston, may be either defined by the piston, as shown, or may be affixed to the uppermost wall 66 of the piston, if desired.

Located within tubular piston 60 is a spring compression assembly including an helical compression spring 61 and a spring guide shaft 62. Spring 61 is made from an alloy which is resistant to corrosion of the liquid with which it contacts and is of sufficient diameter to fit over guide shaft 62, so as to be located between the interior surface of side wall 66 of the piston and the shaft. The spring is of sufficient compressive strength to maintain a liquid tight seal between seal 8 and valve seat 39 at the maximum depth of the liquid being tested. Spring guide shaft 62 is hollow through a sufficient portion to allow spring compression shaft 71, shown in FIG. 4, to travel freely on the inside thereof. Spring compression shaft 71 is a solid rod-like member which contains a metal spring compression pin 79, transversely located thereto. Pin 79 follows grooves 68, formed or machined into guide shaft 62, as the piston cycles through its open and closed positionings. Pin 79 extends beyond the outer diameter of guide shaft 68 a sufficient distance to rest upon the top of spring 61, thus compressing the spring to place a downward bias on the piston as it cycles through its functions. The upper end of spring compression shaft 71, opposite pin 79, is positioned in cap 46 of second tubular casing 40 when the device is fully assembled.

Figure 7:
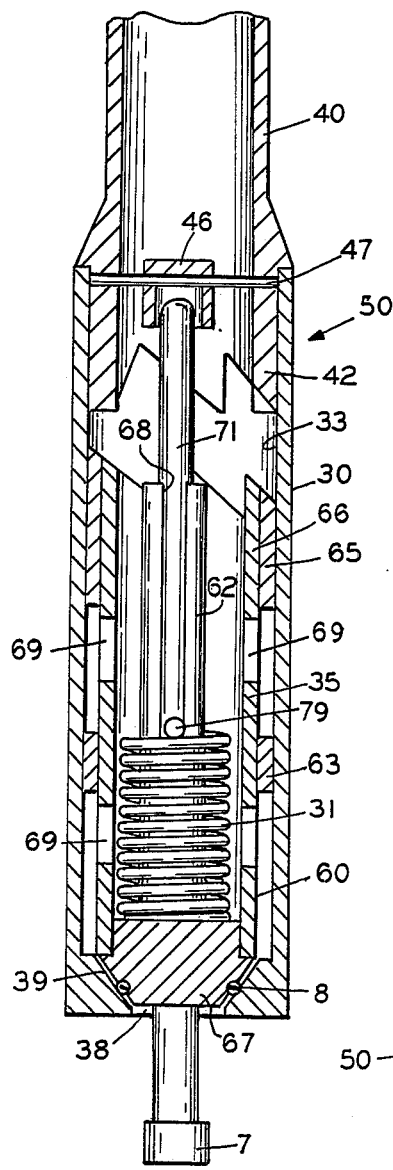
FIG. 7 is a sectional view showing the device in a closed mode.

Referring now the the drawings and to FIGS. 7, 8, and 9, in particular, operation of the device will be described. When pressure is applied against foot 7 of piston 60, the piston retracts into first tubular casing 30. This retraction action breaks the seal between O-ring 8 and valve seat 39 and compresses spring 61 against pin 79 on spring compression shaft 79. The spring compression shaft does not retract, but remains stationary since its upper end is held by the spring compression shaft cap 46.

Figure 8:
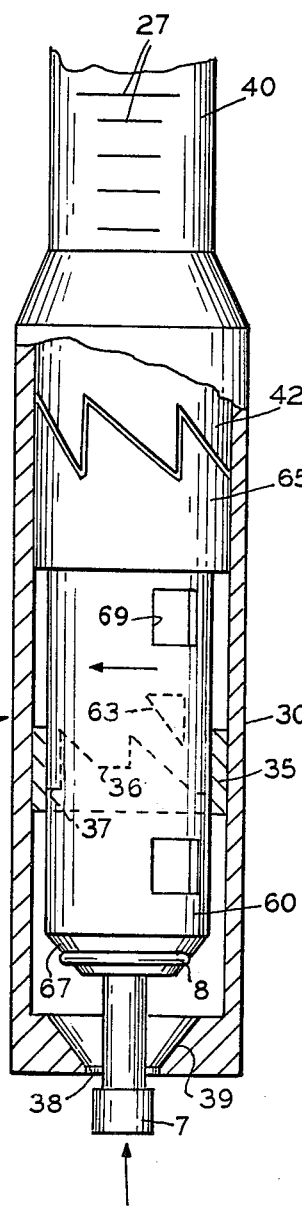
FIG. 8 is a sectional view showing the device during rotation of the piston.

As the piston continues to retract, the caming surfaces of first cam 42 of second casing 40 and second cam 65 of piston 60 interact, causing a rotating action of the piston, as shown in FIG. 8. This rotating action moves the locking lugs 63 of piston 60 from the closed position, shown in FIG. 7, to the open position on the piston caming surface of piston retention means 35 of first tubular casing 30. See also FIG. 3.

Figure 9:
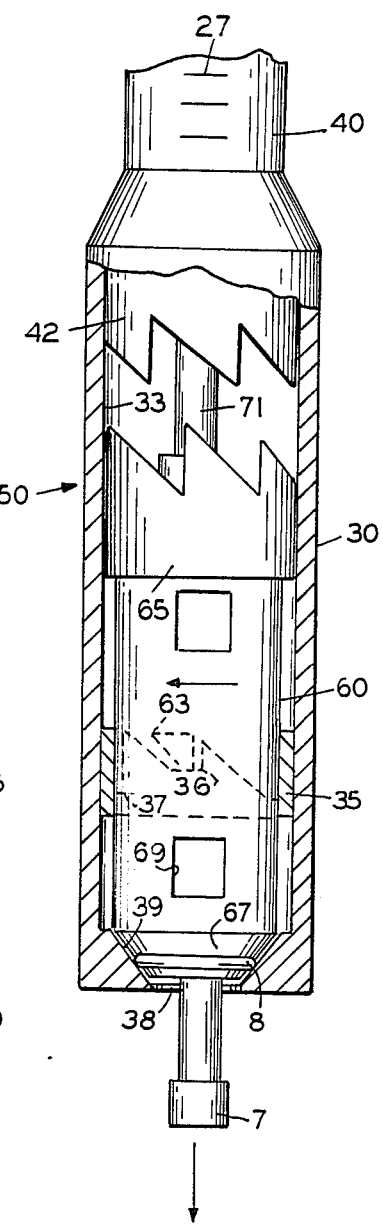
FIG. 9 is a sectional view showing the device in an open mode.

As pressure is released from foot 7, the piston, in its new stage of rotation, travels downward from the pressure of compressed spring 61 until the locking lugs 63 engage lug stops 37 of piston elevation retention means 35, thus holding the piston in the open mode, as shown in FIG. 9. The application of pressure on foot 7 again causes the piston to retract and rotate as described above, moving the locking lugs to a position over the caming surface of piston retention means 35, which will allow the piston to travel downward to the closed position, shown in FIG. 7, with lugs 63 engaging stop lugs 36, shown in FIG. 3. When inward pressure is released from foot 7, once again the O-ring engages the valve seat to prevent flow of liquid either into or out of the device.

If the piston is locked open when the device is lowered into a liquid, as in FIG. 1, the device fills with liquid as it is lowered to the bottom of the tank. When foot 7 reaches the bottom of the tank and pressure is applied to the foot in a downward direction, piston 60 rotates to the closed position and seals the fluid inside device 10 when pressure is released. As the device is removed from the tank it brings with it a profile sample of the fluid level in the tank. Any contaminated liquid, such as water 2, and uncontaminated liquid, such as gasoline 3, maintain their profile within device 10, as in the tank, so that an accurate assessment of amounts of each within the tank can be made, in accordance with measurement marks 27 on the casing. To return the sample to the tank the device is lowered to the tank bottom, downward pressure is applied, and piston 60 rotates to the open position and the liquid exits the device as the device is removed from the tank.

If device 10 is lowered into a liquid tank in the closed position, liquids will not enter until foot 7 contacts the tank bottom and pressure is applied, placing the valve in an open position. Using this approach, tank bottom samples can be obtained without the full profile of the tank. In the example shown in FIG. 1, only a sample of the contaminant, water 2, is thus obtained. Once opened at the bottom of the tank, the device can be immediately closed, thus limiting the size or volume of the bottom sample being retrieved. When device 10 is removed from the liquid tank with the bottom sample, the sample can be removed by pressing inward on foot 7 with the hand or against the inside surface of a sampling container. For storage of the device, after cleaning, threaded couplings 22 are released to separate tubes 21 from one another and from second tubular casing 40. The tubes may then be placed in a carrier for convenient portability. Tubes 21, in the preferred embodiment are approximately forty eight inches in length for storage and portability reasons.

Having thus described in detail a preferred embodiment of the present invention, it is to be appreciated and will be apparent to those skilled in the art that many physical changes could be made in the apparatus without altering the inventive concepts and principles embodied therein. The present embodiment is therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. A liquid sampling and measuring device comprising:
    a tubular casing for holding a liquid, said casing including a liquid conduction port at a lowermost end thereof; and valve means located within said tubular casing, said valve means including a valve seat surrounding said port; a spring biased piston having a seal operable to engage said valve seat for closing said port; a foot member attached to said piston and extending through said port; cam means operable to rotate said piston about its longitudinal axis upon retraction of said piston by pressure on said foot member; and piston retention means for holding said piston in a selected retracted or extended position to open or close said port.

2. The device as described in claim 1 wherein said piston retention means includes a cam member having lug stops at two selected elevations and wherein said piston includes at least one lug affixed thereto, said lug operable to engage a selected lug stop to hold the piston in an open or closed mode relative to said port.

3. The device as described in claim 1 wherein said cam means includes a cam member affixed to said tubular casing above said piston and wherein said cam means further includes a mating cam affixed to said piston, said cam member and mating cam each defining at least one inclined plane operable to engage one another for providing a selected rotation of said piston relative to said tubular casing upon the retraction of said piston by pressure being applied to said foot of said piston.

4. The device as described in claim 1 further comprising a graduated scale for determining the depth of liquid contained within said tubular casing.

5. The device as described in claim 1 wherein said tubular casing is constructed of transparent material for the visual inspection of fluid contained therein.

6. A liquid sampling and measuring device comprising:
    a first tubular casing having a liquid conduction port at a lowermost terminal end thereof and having piston elevation retention means affixed to its interior surface;
    a second tubular casing sealingly engaging said first casing, said second casing having a cam member at a lowermost end thereof;
    a tubular piston located within said first tubular casing, said piston including a bottom wall and cylindrical side wall defining a top opening, the bottom wall provided with port seal means and a foot connected to said bottom wall and extending vertically downward through said port of said first tubular casing and said side wall of said piston provided on its uppermost end with a cam member for engaging said cam member of said second tubular casing for rotation of said piston upon retraction of said piston by pressure upon said foot, and said side wall of said piston provided with one or more lugs for engaging said piston elevation retention means of said first tubular casing to hold said piston in a selected retracted or extended position for opening or closing said port; and
    a compression spring assembly for biasing said piston in a downward port-closing position 7. The device as described in claim 6 wherein said second tubular casing includes spring compression shaft retention means and wherein said spring assembly includes a compression spring and a compression spring shaft, said shaft engaging said spring and said shaft retention means for compressing said spring.

8. The device as described in claim 7 wherein said compression spring is helical in form and contained within said piston and further comprising a spring guide shaft located within said spring for guiding said compression spring shaft relative to said spring.

9. The device as described in claim 6 further comprising one or more extension tubes operable to sealingly engage one another and said second tubular casing.

10. The device as described in claim 9 wherein each of said tubes is constructed of transparent material for viewing the contents thereof.

11. The device as described in claim 9 wherein each of said tubes is provided with measurement marking means.

12. A liquid sampling and measuring device comprising:
    a first tubular casing having a liquid conduction port at a lowermost terminal end thereof and having piston elevation retention means affixed to its interior surface;
    a second tubular casing sealingly engaging said first casing, said second casing having a cam member at a lowermost end thereof and said second casing provided with spring compression shaft retention means;
    a tubular piston located within said first tubular casing, said piston including a bottom wall and cylindrical side wall defining a top opening, the bottom wall provided with port seal mans and a foot connected to said bottom wall and extending vertically downward through said port of said first tubular casing and said side wall of said piston provided on its uppermost end with a cam member for engaging said cam member of said second tubular casing for rotation of said piston upon retraction of said piston by pressure upon said foot, and said side wall of said piston provided with one or more lugs for engaging said piston elevation retention means of said first tubular casing to hold said piston in a selected retracted or extended position for opening or closing said port; and
    a compression spring assembly for biasing said piston in a downward port-closing position, said spring assembly including an helical compression spring, a spring guide shaft located within said spring, and a compression spring shaft, said spring guide shaft provided with a longitudinal groove and said compression spring shaft provided with a transversely oriented compression pin receivable within said groove of said spring guide shaft for longitudinal movement relative thereto, said pin engaging the top of said spring and said compression spring shaft engaging said shaft retention means for compressing said spring.

* * * * *